(12) United States Patent
Eardley et al.

(10) Patent No.: US 10,350,360 B2
(45) Date of Patent: Jul. 16, 2019

(54) DRUG INJECTION DEVICE WITH RESETTABLE MECHANISM ALLOWING PISTON ROD RETRACTION UPON DRUG CARTRIDGE CHANGE

(71) Applicant: Sanofi, Paris (FR)

(72) Inventors: Zoe Georgina Eardley, Warwickshire (GB); Paul Richard Draper, Evesham (GB)

(73) Assignee: Sanofi, Paris (FR)

( * ) Notice: Subject to any disclaimer, the term of this patent is extended or adjusted under 35 U.S.C. 154(b) by 249 days.

(21) Appl. No.: 15/517,875

(22) PCT Filed: Oct. 9, 2015

(86) PCT No.: PCT/EP2015/073443
§ 371 (c)(1),
(2) Date: Apr. 7, 2017

(87) PCT Pub. No.: WO2016/055635
PCT Pub. Date: Apr. 14, 2016

(65) Prior Publication Data
US 2017/0304551 A1  Oct. 26, 2017

(30) Foreign Application Priority Data

Oct. 9, 2014 (EP) ..................... 14306599

(51) Int. Cl.
*A61M 5/20* (2006.01)
*A61M 5/31* (2006.01)
(Continued)

(52) U.S. Cl.
CPC .......... *A61M 5/31543* (2013.01); *A61M 5/20* (2013.01); *A61M 5/24* (2013.01);
(Continued)

(58) Field of Classification Search
CPC .......... A61M 5/31551; A61M 5/31541; A61M 5/31543; A61M 5/31583; A61M 5/31591
See application file for complete search history.

(56) References Cited

U.S. PATENT DOCUMENTS 5,104,380 A * 4/1992 Holman .................. A61M 5/20
604/117
2003/0050609 A1  3/2003 Sams
(Continued)

FOREIGN PATENT DOCUMENTS

WO  WO 2006/126902  11/2006
WO  WO 2013/119132  8/2013

OTHER PUBLICATIONS

International Preliminary Report on Patentability in International Application No. PCT/EP2015/073443, dated Apr. 11, 2017, 8 pages.
(Continued)

*Primary Examiner* — Amber R Stiles
*Assistant Examiner* — Nicholas J Chidiac
(74) *Attorney, Agent, or Firm* — Fish & Richardson P.C.

(57) ABSTRACT

A drug delivery device for selecting and dispensing a number of user variable doses of a medicament. The device comprises a housing, a dose setting element rotatable relative to the housing during dose setting and dose dispensing, a drive member coupled to the dose setting member via a clutch, and a piston rod coupled to the housing and to the drive member. Further, the device further comprises a cartridge holder removably attached to the housing and a reset element, which is axially constrained to the dose setting element, and at least one spring acting on the reset element, such that, if the cartridge holder is detached from the housing, the reset element is axially moved relative to the housing onto a position in which the dose setting element is
(Continued)

rotationally constrained to the housing and the drive member is allowed to rotate relative to the housing.

17 Claims, 4 Drawing Sheets (51) Int. Cl.
 *A61M 5/315* (2006.01)
 *A61M 5/24* (2006.01)
(52) U.S. Cl.
 CPC .... *A61M 5/31541* (2013.01); *A61M 5/31553* (2013.01); *A61M 5/31585* (2013.01); *A61M 5/31593* (2013.01); *A61M 2005/202* (2013.01); *A61M 2005/2407* (2013.01); *A61M 2005/2477* (2013.01); *A61M 2005/2485* (2013.01); *A61M 2005/3126* (2013.01); *A61M 2005/3154* (2013.01); *A61M 2205/581* (2013.01); *A61M 2205/582* (2013.01); *A61M 2205/584* (2013.01)

(56) References Cited

U.S. PATENT DOCUMENTS

| | | |
|---|---|---|
| 2009/0247960 A1 | 10/2009 | Kohlbrenner et al. |
| 2011/0224622 A1 | 9/2011 | Karlsson |
| 2012/0136315 A1 | 5/2012 | Wieselblad et al. |
| 2012/0209212 A1* | 8/2012 | Plumptre .......... A61M 5/31543 604/207 |
| 2013/0096513 A1 | 4/2013 | Smith |
| 2016/0129196 A1* | 5/2016 | Hirschel .......... A61M 5/31541 604/211 |
| 2017/0173268 A1* | 6/2017 | Enggaard ................ A61M 5/20 |

OTHER PUBLICATIONS

International Search Report and Written Opinion in International Application No. PCT/EP2015/073443, dated Dec. 17, 2015, 12 pages.

* cited by examiner

DRUG INJECTION DEVICE WITH RESETTABLE MECHANISM ALLOWING PISTON ROD RETRACTION UPON DRUG CARTRIDGE CHANGE

CROSS-REFERENCE TO RELATED APPLICATIONS

This application is a U.S. national stage application under 35 USC § 371 of International Application No. PCT/EP2015/073443, filed on Oct. 9, 2015, which claims priority to European Patent Application No. 14306599.3 filed on Oct. 9, 2014, the entire contents of which are incorporated herein by reference.

TECHNICAL FIELD

The present disclosure is generally directed to a drug delivery device for selecting and dispensing a number of user variable doses of a medicament, and a method of assembling same.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present disclosure is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without subverting the device itself. Consequently, such disposable devices need not have a resettable dose setting mechanism. The present disclosure is directed to reusable devices which allow resetting of the device and a replacement of a cartridge. Resetting of the device typically involves moving a piston rod or lead screw from an extended (distal) position, i.e. a position after dose dispensing, into a more retracted (proximal) position.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

SUMMARY

Manually driven reusable drug delivery devices are known e.g. from WO 2014/033195 A1 and EP 2 274 030 B1. These devices comprise a last dose mechanism preventing setting of a dose which exceeds the amount of medicament remaining in the cartridge. Replacing a cartridge allows resetting of this last dose mechanism by pushing the piston rod in a direction opposite to the dispensing direction.

Further, EP 1 819 382 B1 discloses a spring driven drug delivery device with a housing, a dose setting element rotatable relative to the housing during dose setting and dose dispensing between a minimum dose position and a maximum dose position, a drive member coupled to the dose setting member via a ratchet, and a piston rod threaded to a housing insert and rotationally constrained to the drive member. Resetting of the device is mentioned in this document differing from the above definition as the process of reducing a set dose. Replacing a cartridge and resetting e.g. the piston rod is not disclosed in EP 1 819 382 B1.

Some aspects of the disclosure can be implemented to provide an improved resettable drug delivery device.

A drug delivery device according to the present disclosure is suitable for selecting and dispensing a number of user variable doses of a medicament. The device typically comprises a housing, a dose setting element, a drive member coupled to the dose setting member via a clutch and a piston rod coupled to the housing and to the drive member. Preferably, the dose setting member is rotatable relative to the housing during dose setting, i.e. increasing or decreasing the dose, and dose dispensing between a minimum dose position and a maximum dose position. The drive member may be rotationally coupled to the dose setting member via a slipping clutch during dose setting and rotationally constrained to the dose setting member during dose dispensing. The present disclosure is based on the idea of providing a cartridge holder removably attached to the housing and a reset element. The reset element is preferably axially constrained to the dose setting element. In addition, the device may comprise at least one spring acting on the reset element, such that, if the cartridge holder is detached from the housing, the reset element is axially moved relative to the housing into a position in which the drive member is allowed to rotate relative to the housing. Preferably, the reset element is axially moved relative to the housing into a position in which the dose setting element is rotationally constrained to the housing. In other words, detachment of the cartridge holder from the housing allows an axial movement of the reset element and, preferably, the dose setting element into a resetting position, in which the drive member may be rotated relative to the housing and relative to the dose setting member. As the piston rod is coupled to the housing and to the drive member, e.g. via a threaded interface with the housing or a housing insert and a splined interface with the drive member, resetting of the piston rod requires free rotation of the drive member. Thus, resetting of the drug delivery device may be performed simply by pushing back the piston rod or lead screw after removal of the cartridge holder.

If the cartridge holder is attached to the housing, the cartridge holder preferably moves the reset element and the dose setting element against the bias of the at least one spring into a position in which the dose setting element is rotatable relative to the housing. Thus, attachment of the cartridge holder locks the device in a dose setting and dose dispensing mode allowing dose setting and dose dispensing which requires rotation of the dose setting element relative to the housing.

In a preferred embodiment, the reset element is permanently rotationally constrained to the housing. This allows the reset element to rotationally lock or unlock (constrain or unconstrain) component parts to the housing by engaging or disengaging the reset element with component parts. The axial movement of the reset element between the resetting mode and the dose setting and dose dispensing mode may be used to couple or decouple component parts to or from the housing.

According to an embodiment the drive member is axially movable relative to the housing between a dose setting position in which the drive member is rotationally constrained to the housing via the reset element and a dose dispensing position in which the drive member is rotatable relative to the reset element and the housing. In other words, the axial position of the drive member determines whether the device is in a dose setting mode allowing a user to increase or decrease a dose by rotation of the dose setting member without dispensing medicament or in a dose dispensing mode allowing a user to dispense a set dose by rotation of the dose setting element and the drive member. Preferably, the at least one spring biases the drive member into its dose setting position.

In a further development of this embodiment, the clutch between the dose setting element and the drive member is a slipping clutch with first clutch teeth on the drive member and second clutch teeth on a clutch plate, which is rotationally constrained to the dose setting element during dose setting and dose dispensing. For example, the first and/or second clutch teeth may each be distributed as a ring of teeth, preferably facing in the axial direction. The clutch features and the corresponding clutch features may each comprise a series of teeth, preferably saw-teeth, which are allowed to slip over each other if not pressed against each other too firmly. In other words, the clutch features may be overhauled against the axial bias of a clutch spring by allowing the sleeve and/or the clutch element to translate axially against the force of the clutch spring. This may result in an oscillating axial movement of the sleeve and/or the clutch element due to continued disengagement and following re-engagement into the next detented position. An audible click may be generated by this re-engagement, and tactile feedback may be given by the change in torque input required.

The at least one spring may bias the drive member into abutment with the clutch plate. If the cartridge holder is detached from the housing, the at least one spring may bias the dose setting element into an axial position relative to the clutch plate in which the clutch plate and the dose setting element are rotationally de-coupled. This allows rotation of the drive member relative to the dose setting element without overcoming the slipping clutch.

Preferably, the clutch between the drive member and the dose setting element is a slipping clutch which allows relative rotation between the drive member and the dose setting element in both directions during dose setting for increasing or decreasing a set dose. If the device is a spring driven device, the clutch teeth may be designed to provide a different resistance for overcoming the clutch depending on the direction of the relative rotation. For example, the ramp angle may be shallower resulting in a lower resistance in the dose increasing direction and steeper resulting in a higher resistance in the dose decreasing direction.

The housing may comprise an inwardly protruding wall or web with a central opening and at least one further opening with one of the cartridge holder and the reset element comprising at least one axially extending finger or the like protrusion extending through the further opening. This allows imparting a force or movement from the cartridge holder to the reset element or vice versa. Preferably, the inwardly protruding wall or web comprises an inner thread wherein the piston rod is rotationally constrained to the drive member and comprises an outer thread engaging the inner thread.

The drug delivery device may further comprise at least one cartridge holder spring axially interposed between the cartridge holder and the inwardly protruding wall or web. This additional spring may compensate length tolerances of the cartridge and further bring the cartridge in a defined distal position.

According to a preferred embodiment, the drug delivery device is a spring driven device. A drive spring, preferably a torsion spring, may be interposed between the housing and the dose setting element. Providing a resilient drive member, such as a torsion spring, generating the force or torque required for dose dispensing reduces the user applied forces for dose dispensing. This is especially helpful for users with impaired dexterity. In addition, the dial extension of the known manually driven devices, which is a result of the required dispensing stroke, may be omitted by providing the resilient member because merely a small triggering stroke may be necessary for releasing the resilient member. The drive spring may be pre-charged, at least partly, and/or may be charged by a user during dose setting.

In another preferred embodiment, the drug delivery device further comprises a gauge element radially interposed between the housing and the dose setting element. The gauge element is axially movable relative to the housing and in threaded engagement with the dose setting element. The housing may comprise at least one aperture and the gauge element may comprise at least one aperture. If the dose setting element is a number sleeve which comprises markings on its outer surface, at least one of the markings is visible through the aperture in the gauge element and the aperture in the housing during dose setting and dose dispensing. The term aperture may include a simple opening in the housing or gauge element or a transparent window or lens. A window in the housing may be incorporated using a 'twin-shot' moulding technology. For example, the housing is moulded during a 'first shot' in a translucent material, and the outer cover of the housing is moulded during a 'second shot' in an opaque material.

The gauge element may be axially guided within the housing such that rotation of the dose setting element causes an axial displacement of the gauge element. The position of the gauge element may thus be used to identify the actually set and/or dispensed dose. Different colours of sections of the gauge member may facilitate identifying the set and/or dispensed dose without reading numbers, symbols or the like on a display. As the gauge element is in threaded engagement with the dose setting element, rotation of the dose setting element causes an axial displacement of the gauge element relative to the dose setting element and relative to the housing. The gauge element may have the form of a shield or strip extending in the longitudinal direction of the device. As an alternative, the gauge element may be a sleeve. In an embodiment, the dose setting element is marked with a sequence of numbers or symbols arranged on a helical path. With the dose setting element located radially inwards of the gauge element, this allows that at least one of the numbers or symbols on the dose setting element is visible through the aperture or window. In other words, the gauge element may be used to shield or cover a portion of the dose setting element and to allow viewing onto only a limited portion of the dose setting element. This function may be in addition to the gauge element itself being suitable for identifying or indicating the actually set and/or dispensed dose.

In general, the concept of the gauge element and the dose setting element is applicable for various types of devices with or without a drive spring. In a preferred embodiment, the dose setting element, during dose setting, is adapted to undergo a mere rotational movement within the housing and relative to the housing. In other words, the dose setting element does not perform a translational movement during dose setting. This avoids that the dose setting element is wound out of the housing or that the housing has to be lengthened to cover the dose setting element within the housing.

The relative movements of the gauge element and the dose setting element may further be used to define the minimum dose position and the maximum dose position. Typically, the minimum settable dose is zero (0 IU of insulin formulation), such that the limiter stops the device at the end of dose dispensing. The maximum settable dose, for example 60, 80 or 120 IU of insulin formulation, may be limited to reduce the risk of overdosage and to avoid the additional spring torque needed for dispensing very high doses, while still being suitable for a wide range of patients needing different dose sizes. Preferably, the limits for the minimum dose and the maximum dose are provided by hard stop features. For example, the gauge element comprises a minimum dose rotational stop and a maximum dose rotational stop and the dose setting element comprises a minimum dose rotational counter stop and a maximum dose rotational counter stop. Abutment of the respective stop and counter stop blocks further relative movement between the gauge element and the dose setting element. As the dose indicator rotates relative to the gauge element during dose setting and during dose dispensing, these two components are suitable to form a reliable and robust limiter mechanism.

The device may further comprise a dispensing button or trigger. The button is preferably a user operable element located proximally of the drive sleeve and the clutch element. When used in a drug delivery device, the button may extend from the proximal end of the device and, preferably, does not change its axial position during dose setting. The button is preferably coupled to a user operable dose selector and may be releasably coupled to a number sleeve component and/or a stationary housing component. In an alternative embodiment, the button may be part of a dose setting arrangement or may be the dose setting member. The button may be a multi-functional element having in addition to the above features e.g. a clicker feature.

The stationary housing component is a fixed basis for relative movements of the axially movable (drive) sleeve, the clutch element and the button. It may be part of a multi-component housing or may be the only housing component of a drug delivery device. The housing component may be a multi-functional element having in addition to the above features e.g. a clicker feature and/or an interface to the piston rod.

The drug delivery device may further comprise a last dose protection mechanism for preventing the setting of a dose, which exceeds the amount of liquid left in a cartridge. This has the advantage that the user knows how much will be delivered before starting the dose delivery. It also ensures that dose delivery stops in a controlled manner without the bung entering the neck portion of the cartridge where the diameter is smaller which may result in an underdose. For example, the last dose protection mechanism comprises a nut member interposed between the drive member and the dose setting element (number sleeve) or any other component which rotates during dose setting and dose dispensing. In a preferred embodiment, the dose setting element rotates during dose setting and during dose dispensing, whereas the drive member only rotates during dose dispensing together with the dose setting element. Thus, in this embodiment, the nut member will only move axially during dose setting and will remain stationary with respect to these components during dose dispensing. Preferably, the nut member is threaded to the drive member and splined to the dose setting member. As an alternative, the nut member may be threaded to the dose setting member and may be splined to the drive member. The nut member may be a full nut or a part thereof, e.g. a half nut.

The injection device may comprise at least one clicker mechanism for generating a tactile and/or audible feedback. A feedback may be generated during dose setting (increasing and/or decreasing a dose), dose dispensing and/or at the end of dose dispensing.

The drug delivery device may comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Non-limiting, exemplary embodiments will now be described with reference to the accompanying drawings, in which.

DETAILED DESCRIPTION

Figure 1:
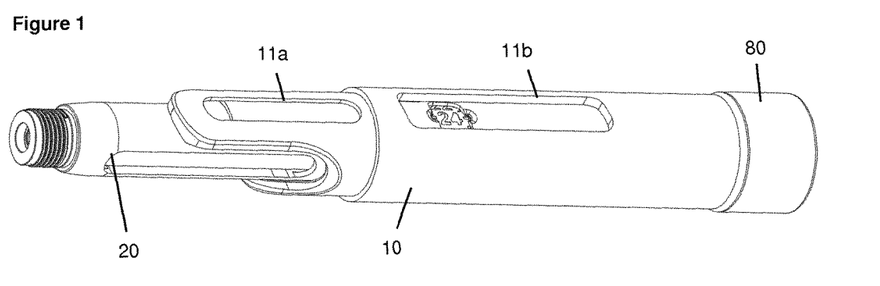
FIG. 1 shows a top view of the drug delivery device.
Figure 2:
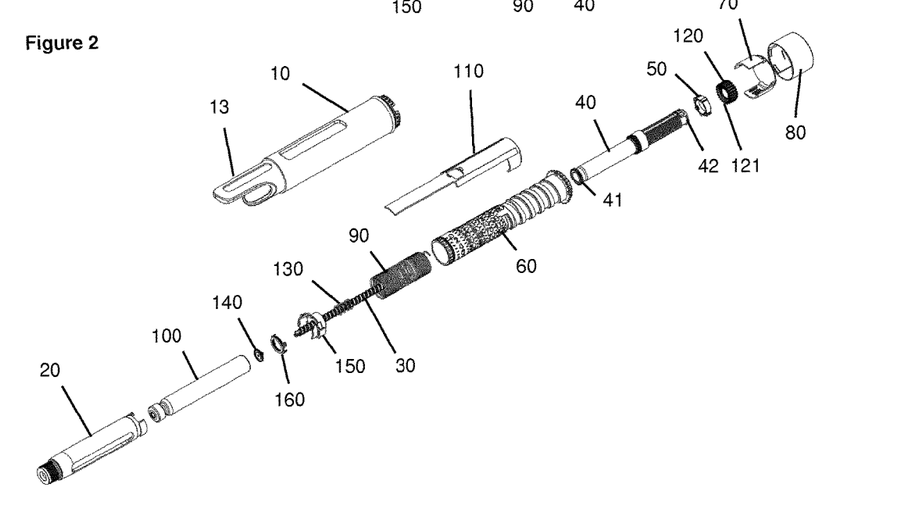
FIG. 2 shows an exploded view of the components of the device of FIG. 1.
Figure 3:
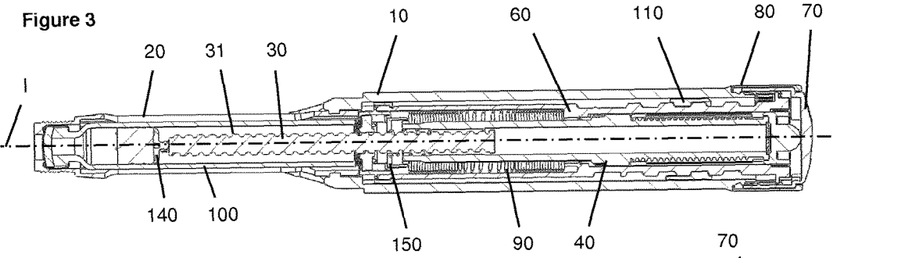
FIG. 3 shows a sectional view of the device of FIG. 1.

FIG. 1 shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or housing 10, a cartridge holder 20, a lead screw (piston rod) 30, a drive sleeve 40, a nut 50, a dose setting element which is a dose indicator (number sleeve) 60, a button 70, a dial grip or dose selector 80, a torsion spring 90, a cartridge 100, a gauge element 110, a clutch plate 120, a clutch spring 130, a bearing 140, a reset plate 150 and a cartridge holder spring 160. A needle arrangement (not shown) with a needle hub and a needle cover may be provided as additional components, which can be exchanged as explained above. All components are located concentrically about a common principal axis I of the mechanism which is shown in FIG. 3.

The housing 10 or body is a generally tubular element having a proximal end with an enlarged diameter. The housing 10 provides location for the liquid medication cartridge 100 and cartridge holder 20, windows 11a, 11b for viewing the dose number on the dose indicator 60 and the gauge element 110, and a feature on its external surface, e.g. a circumferential groove, to axially retain the dose selector 80. It is also possible in another embodiment to have one large window. Then the opaque bridge between windows 11a and 11b is replaced by a transparent area. A flange-like or cylindrical inner wall 12 comprises an inner thread engaging the piston rod 30. The housing 10 further has at least one internal, axially orientated slot or the like for axially guiding the gauge element 110. In the embodiment shown in the Figures, the distal end is provided with an axially extending strip 13 partly overlapping cartridge holder 20. The Figures depict the housing 10 as a single housing component. However, the housing 10 could comprise two or more housing components which may be permanently attached to each other during assembly of the device.

The cartridge holder 20 is located at the distal end of housing 10 and attached thereto in a releasable manner. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10. The cartridge holder 20 contains the replaceable cartridge 100 and acts to axially align the reset plate 150 spline teeth 151 with the drive sleeve 40 spline teeth 41. When the cartridge holder 20 is removed, the trigger spring 130 forces the reset plate 150 (and dose setting element 60) axially in a distal direction, disengaging the spline teeth 41, 151 between the reset plate 150 and the drive sleeve 40 and the spline teeth between the clutch plate 120 and the dose setting element 60, allowing the device to be reset.

The piston rod 30 is rotationally constrained to the drive sleeve 40 via a splined interface. When rotated, the piston rod 30 is forced to move axially relative to the housing 10, through its threaded interface with the housing 10.

Figure 7A:
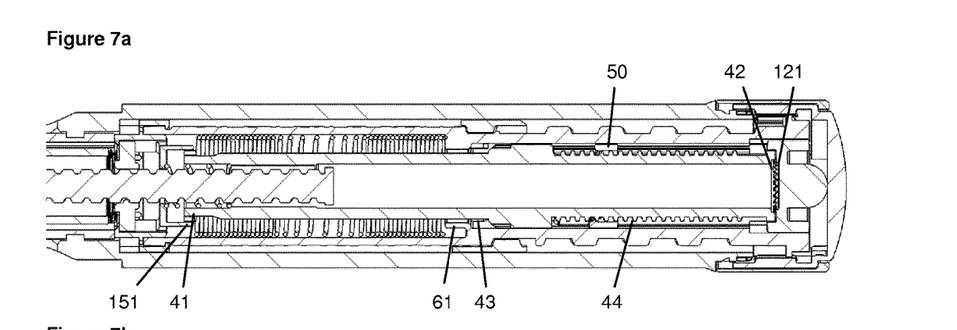
FIGS. 7a, b show in a sectional view the device of FIG. 1 in the dose setting mode and in the dose dispensing mode.
Figure 7B:
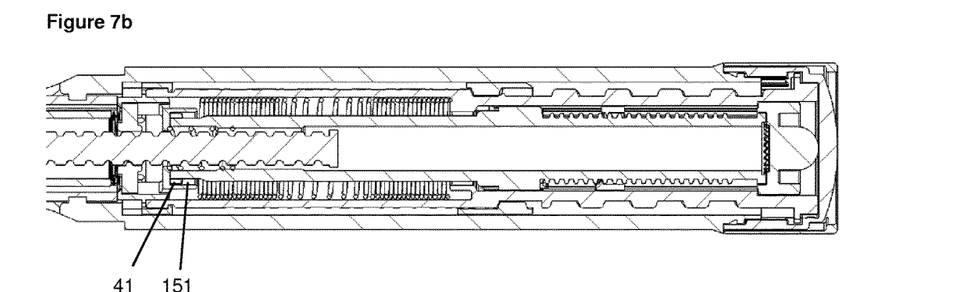

The drive sleeve 40 extends from the interface 42, 121 with the dose setting element 60 (via the clutch plate 120) down to a splined tooth interface 41, 151 (FIG. 6) with the reset plate 150. This provides a rotational constraint to the drive sleeve 40 during dose setting. When the button 70 is pressed, these spline teeth 41, 151 are disengaged allowing the drive sleeve 40 to rotate under the action of the drive spring 90, dispensing the set dose. Pressing the button 70 also engages an additional spline clutch 43, 61 (FIG. 7a) between the drive sleeve 40 and dose setting element 60.

The last dose nut 50 is located between the dose setting element 60 and the drive sleeve 40. It is rotationally constrained to the dose setting element 60, via a splined interface. It moves along a helical path relative to the drive sleeve 40, via a threaded interface 44, when relative rotation occurs between the dose setting element 60 and drive sleeve 40 (during dialling and resetting only).

Figures 4, 5, 6:
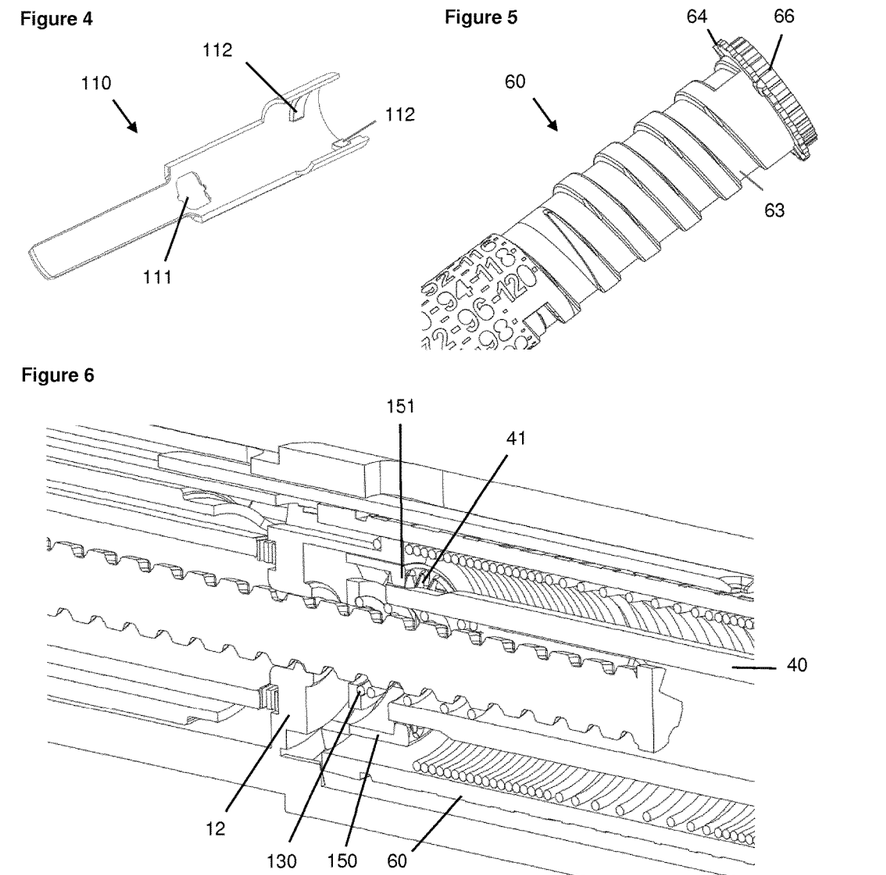
FIG. 4 shows a side view of the gauge element of the device of FIG. 1.
FIG. 5 shows a detail of the number sleeve of the device of FIG. 1.
FIG. 6 shows in a sectional view a detail of the device of FIG. 1.
Figure 12A:
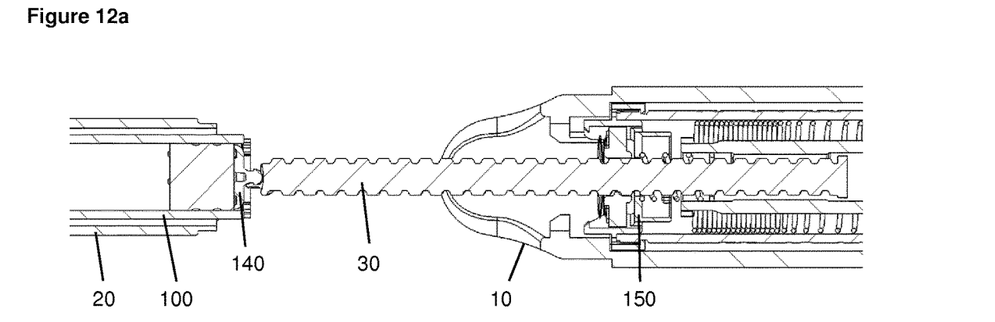
FIGS. 12a-c show in sectional views the sequence of resetting the device of FIG. 1.
Figure 12B:
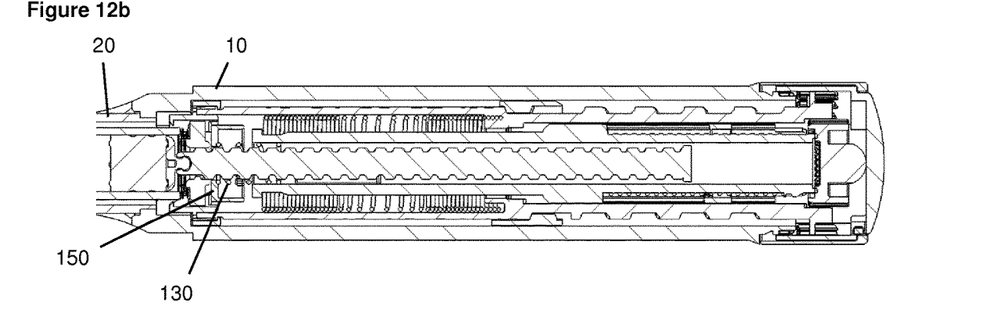
Figure 12C:
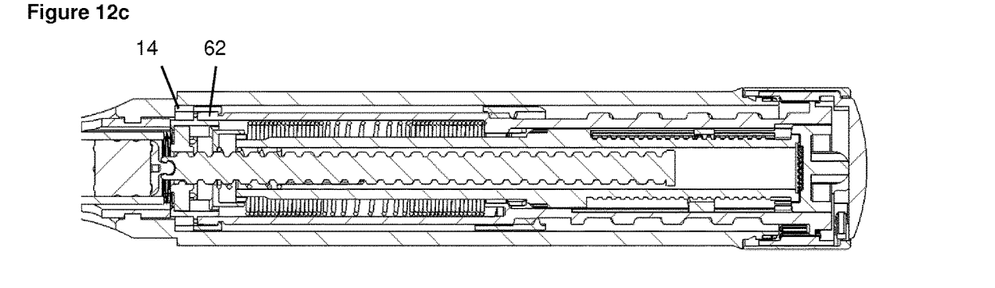

The dose setting element 60 is constrained, via a clip at its distal end, to the reset plate 150 to allow rotation but not axial translation when in the dialling and dispense conditions. On entry to the reset condition the reset plate 150 and dose setting element 60 move axially in the distal direction, engaging a spline interface 62, 14 between the dose setting element 60 and the housing 10 to prevent rotation during reset (FIGS. 12a to 12c). As shown in FIG. 5, the dose setting element 60 is marked with a sequence of numbers, which are visible through opening 111 (FIG. 4) in the gauge element 110 and the slot-like window 11b in the housing 10, to denote the dialled dose of medicament.

The button 70 is splined to the dose setting element 60 when in the dose dialling condition. This spline interface is disconnected when the button 70 is pressed to trigger a dispense.

The dose selector 80 is radially constrained to the housing 10 and rotationally constrained to the button 70. When depressed, the button 70 is rotationally constrained to the housing 10 via a splined engagement.

The drive spring 90 is attached at one end to the housing 10 and at the other end to the dose setting element 60. The drive spring 90 is pre-wound upon assembly, such that it applies a torque to the dose setting element 60 when the mechanism is at zero count dialled. The action of rotating the dose selector 80, to set a dose, rotates the dose setting element 60 relative to the housing 10, and charges the drive spring 90.

The gauge element 110 is constrained to prevent rotation but allow translation relative to the housing 10 via a splined interface. The gauge element 110 has helical features 112 on its inner surface which engage with the helical thread 63 formed in the dose setting element 60 such that rotation of the dose setting element 60 causes axial translation of the gauge element 110. These helical features on the gauge element 110 also create stop abutments against the ends of the helical cut (thread) in the dose setting element 60 to limit the minimum and maximum dose that can be set.

The clutch plate 120 is splined to the dose setting element 60 when in the dialling and dispense conditions. On entry to the reset condition the dose setting element 60 moves axially in a distal direction, disconnecting this spline interface with the clutch plate 120. The clutch plate 120 is also coupled to the drive sleeve 40 via a ratchet interface 42, 121 (FIG. 7a), which occurs on an axial abutment. The ratchet provides a detented position between the dose setting element 60 and drive sleeve 40 corresponding to each dose increment, and engages different ramped tooth angles during clockwise and anti-clockwise relative rotation.

Figure 8A:
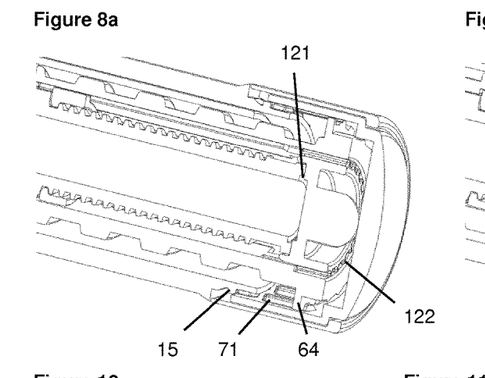
FIGS. 8a, b show details of FIGS. 7a, b.
Figure 8B:
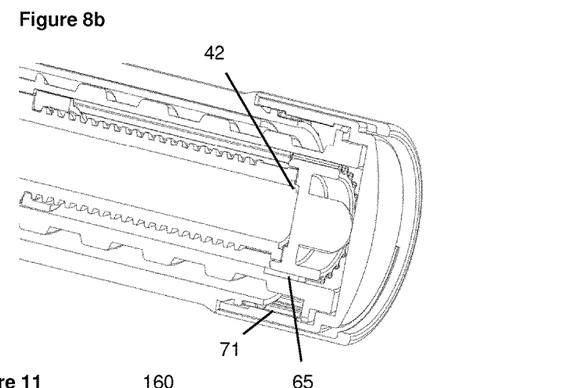

The relative axial positions of the drive sleeve 40, clutch plate 120 and button 70 are influenced by the action of the trigger spring 130, which applies a biasing force on the drive sleeve 40 in the proximal direction. In the at rest position, this ensures that splines 71 of the button 70 are engaged with splines 64 of the dose setting element 60 and that the drive sleeve 40 teeth 41 are engaged with teeth 151 of the reset plate 150 (FIGS. 8a, 8b).

The bearing 140 is axially constrained to the piston rod 30 and acts on the bung within the liquid medicament cartridge 100.

The reset plate 150 is rotationally splined to the housing 10 and biased in a distal direction against the cartridge holder 20 by the trigger spring 130. The reset plate 150 contains spline teeth 151 that prevent rotation of the drive sleeve 40 during dialling of the device, and clips to prevent axial motion of the dose setting element 60 in the dialling and dispense conditions. The reset plate 150 clips into the housing 10 to limit its range of motion in the proximal direction.

The cartridge holder spring 160 acts between the housing 10 and the cartridge 100 to bias the cartridge 100 in the distal direction.

The main functions of the device are now described in more detail: With the device in the at rest condition as shown in FIG. 3, the dose setting element 60 is positioned against its zero dose abutment with the gauge element 110, and the button 70 is not depressed. Dose marking '0' on the dose setting element 60 is visible through the window 11b of the housing 10 and gauge element 110. The drive spring 90, which has a number of pre-wound turns applied to it during assembly of the device, applies a torque to the dose setting element 60 and is prevented from rotating by the zero dose abutment. It is also possible to "back-wind" the mechanism slightly due to an offset between the zero dose stop and the angular offset of the drive sleeve spline teeth 41. This has the effect of preventing possible weepage when a dose is dialled and the zero dose abutment is disengaged.

The user selects a variable dose of liquid medicament by rotating the dose selector 80 clockwise, which generates an identical rotation in the dose setting element 60. Rotation of the dose setting element 60 causes charging of the drive spring 90, increasing the energy stored within it. As the dose setting element 60 rotates, the gauge element 110 translates axially due to its threaded engagement 63, 112 thereby showing the value of the dialled dose. The gauge element 110 has opaque surfaces (flanges) either side of the window area 111 which cover the numbers printed on the dose setting element 60 adjacent to the dialled dose to ensure only the set dose number is made visible to the user.

One specific element of this mechanism is inclusion of a visual feedback feature in addition to the discrete dose number display typical on devices of this type. The distal end of the gauge element 110 creates a sliding scale (although this could be formed using a separate component engaged with the dose setting element 60 on a different helical track if desired) through the small window 11a in the housing 10. As a dose is set by the user the gauge element 110 translates axially, the distance moved proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge element 110 feature provides feedback to the user during dispense regarding dispense progress without the need to read the dose number itself.

The gauge element 110 display may be formed by an opaque sliding element revealing a contrasting coloured component underneath. Alternatively, the concealed component may be printed with coarse (occasional) dose numbers or other indices to provide more precise resolution. In addition, the gauge element 110 display simulates a syringe action during dose set and dispense.

The drive sleeve 40 is prevented from rotating as the dose is set due to the engagement of its splined teeth 41 with the reset plate 150, and the clutch plate 120 is rotated due to the engagement of its splined teeth 122 with teeth 65 of the dose setting element 60 (FIGS. 8a, 8b). Relative rotation must therefore occur between the clutch plate 120 and drive sleeve 40 via the ratchet interface 121, 42.

The user torque required to rotate the dose selector 80 is a sum of the torque required to wind up the drive spring 90, and the torque required to overhaul the ratchet feature. The trigger spring 130 is designed to provide an axial force to the ratchet feature and to bias the clutch plate 120 onto the drive sleeve 40. This axial load acts to maintain the ratchet teeth engagement of the clutch plate 120 and drive sleeve 40. The torque required to overhaul the ratchet in the dose set direction is a function of the axial load applied by the trigger spring 130, the clockwise ramp angle of the ratchet, the friction coefficient between the mating surfaces and the mean radius of the ratchet features.

As the user rotates the dose selector 80 sufficiently to increment the mechanism by 1 increment, the clutch plate 120 rotates relative to the drive sleeve 40 by 1 ratchet tooth 121, 42. At this point the ratchet teeth re-engage into the next detented position. An audible click is generated by the ratchet re-engagement, and tactile feedback is given by the change in torque input required.

Relative rotation of the dose setting element 60 and the drive sleeve 40 causes the last dose nut 50 to travel along its threaded path, towards its last dose abutment on the drive sleeve 40.

With no user torque applied to the dose selector 80, the dose setting element 60 is now prevented from rotating back under the action of the drive spring 90, solely by the ratchet engagement 121, 42 between the clutch plate 120 and the drive sleeve 40. The torque necessary to overhaul the ratchet 121, 42 in the anti-clockwise direction is a function of the axial load applied by the trigger spring 130, the anti-clockwise ramp angle of the ratchet, the friction coefficient between the mating surfaces and the mean radius of the ratchet features. The torque necessary to overhaul the ratchet must be greater than the torque applied to the dose setting element 60 (and hence clutch plate 120) by the drive spring 90. The ratchet ramp angle is therefore increased in the anti-clockwise direction to ensure this is the case whilst ensuring the dial-up torque is acceptably low.

The user may now choose to increase the selected dose by continuing to rotate the dose selector 80 in the clockwise direction. The process of overhauling the ratchet interfaces 121, 42 between the dose setting element 60 and drive sleeve 40 is repeated for each dose increment. Additional energy is stored within the drive spring 90 for each dose increment and audible and tactile feedback is provided for each increment dialled by the re-engagement of the ratchet teeth. The torque required to rotate the dose selector 80 increases as the torque required to wind up the drive spring 90 increases. The torque required to overhaul the ratchet in the anti-clockwise direction must therefore be greater than the torque applied to the dose setting element 60 by the drive spring 90 when the maximum dose has been reached.

If the user continues to increase the selected dose until the maximum dose limit is reached, the dose setting element 60 engages with its maximum dose abutment on the gauge element 110 (FIGS. 4 and 5). This prevents further rotation of the dose setting element 60, clutch plate 120 and dose selector 80.

Depending on how many increments (counts) have already been delivered by the mechanism (cartridge), during selection of a dose, the last dose nut 50 may contact its last dose abutment with the drive sleeve 40. The abutment prevents further relative rotation between the dose setting element 60 and the drive sleeve 40, and therefore limits the dose that can be selected. The position of the last dose nut 50 is determined by the total relative rotation between the dose setting element 60 and drive sleeve 40, that has accumulated each time the user has set a dose.

With the mechanism in a state in which a dose has been selected, the user is able to deselect any number of increments from this dose (dose correction). Deselecting or decreasing a dose is achieved by the user rotating the dose selector 80 anti-clockwise. The torque applied to the dose selector 80 by the user is sufficient, when combined with the torque applied by the drive spring 90, to overhaul the ratchet 121, 42 between the clutch plate 120 and drive sleeve 40 in the anti-clockwise direction. When the ratchet is overhauled, anti-clockwise rotation occurs in the dose setting element 60 (via the clutch plate 120), which returns the dose setting element 60 towards the zero dose position, and unwinds the drive spring 90. The relative rotation between the dose setting element 60 and drive sleeve 40 causes the last dose nut 50 to return along its helical path, away from the last dose abutment.

With the mechanism in a state in which a dose has been selected, the user is able to activate the mechanism to commence delivery of a dose. Delivery of a dose is initiated by the user depressing the button 70 axially.

When the button 70 is depressed, splines 64, 71 between the button 70 and dose setting element 60 are disengaged, rotationally disconnecting the button 70 and dose selector 80 from the delivery mechanism. Splines 71 on the button 70 also engage with splines 15 on the housing 10 (so that the dose selector 80 and button 70 do not rotate during dispense—see FIGS. 8a and 8b). The button 70 force acts on the drive sleeve 40, via the clutch plate 120, which travels axially and disconnects the splined engagement with the reset plate 150, allowing rotation of the drive sleeve 40. The force on the clutch plate 120 to drive sleeve 40 ratchet is increased by compression of the trigger spring 130, causing these components to spin together rather than overhaul the ratchet 121, 42, driven by the drive spring 90 via the dose setting element 60. Rotation of the drive sleeve 40 causes the piston rod 30 to rotate due to their splined engagement, and the piston rod 30 then advances due to its threaded engagement to the housing 10. The dose setting element 60 rotation also causes the gauge element 110 to traverse axially back to its zero position whereby the zero dose abutment stops the mechanism. During dispense an additional splined interface 43, 61 between the drive sleeve 40 and dose setting element 60 is engaged to prevent free rotation of the dose setting element 60 if the button 70 force is removed part way through a dispense, where the clutch plate 120 to drive sleeve 40 ratchet may be momentarily unloaded before the drive sleeve 40 re-establishes its rotational engagement with the reset plate 150 splines.

Figure 9:
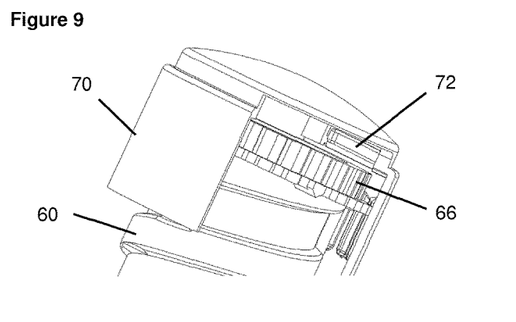
FIG. 9 shows a detail of the device of FIG. 1.
Figure 10:
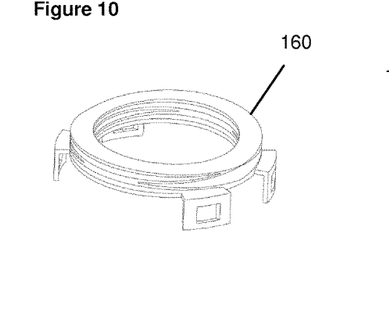
FIG. 10 shows a side view of the cartridge holder spring of the device of FIG. 1.
Figure 11:
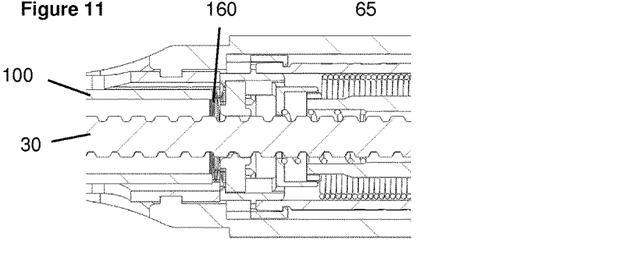
FIG. 11 shows a detail of the device of FIG. 1.

Tactile feedback during dose dispense is provided via a compliant cantilever clicker arm 72 integrated into the button 70 (FIG. 9). This interfaces radially with ratchet features 66 on the dose setting element 60. During dispense, as the dose setting element 60 rotates and the button 70 is rotationally coupled to the housing 10, the features 66 interact with the clicker arm 72 to produce an audible click with each dose increment (dose count) delivered.

Delivery of a dose continues via the mechanical interactions described above while the user continues to depress the button 70. If the user releases the button 70, the trigger spring 130 returns the button 70 to its at rest position via the drive sleeve 40 and clutch plate 120, the drive sleeve 40 becomes rotationally constrained to the reset plate via clutch teeth 41, 151 and delivery of a dose is halted.

During delivery of a dose, the drive sleeve 40 and dose setting element 60 rotate together, so that no relative motion in the last dose nut 50 occurs. The last dose nut 50 therefore travels axially along the drive sleeve 40 only during dialling (and reset).

Once the delivery of a dose is stopped by the dose setting element 60 returning to the zero dose abutment, the user may release the button 70, which will re-engage the drive sleeve 40 spline teeth 41, 151 with the reset plate 150. The mechanism is now returned to the at rest condition.

The mechanism also contains a cartridge holder spring 160 which acts on the rear face (rim) of the cartridge 100 to bias it in a distal direction. This aids dose accuracy as it ensures the cartridge 100 is always biased distally, removing the effect of the tolerance on the cartridge 100 length and the possibility of the cartridge 100 moving proximally when a needle is fitted to the device. In the embodiment shown, the cartridge holder spring 160 consists of a wave spring component, but it may equally be any spring means.

It is possible to angle the spline teeth 41, 151 on either the drive sleeve 40 or reset plate 150 so that when the button 70 is released the re-engagement of the spline teeth fractionally backwinds the drive sleeve 40 thereby removing the engagement of the dose setting element 60 to the gauge element 110 zero dose stop abutment. This compensates for the effect of clearances in the mechanism (for example due to tolerances) which could otherwise lead to slight advancement of the piston rod 30 and medicament dispense when the device is dialled for the subsequent dose (due to the dose setting element 60 zero dose stop no longer controlling the mechanism and instead the control returning to the splines between the drive sleeve 40 and housing 10).

To reset the mechanism, the user first unscrews the cartridge holder 20, which allows the trigger spring 130 to move the reset plate 150 (and consequently the dose setting element 60) axially in a distal direction (FIG. 12a). This axial travel is sufficient to disconnect the splines 41, 151 between the reset plate 150 and the drive sleeve 40 and the splines 122, 65 between the clutch plate 120 and the dose setting element 60. It also removes some compression from the trigger spring 130. Simultaneously, an engagement is made between spline teeth 14, 62 on the dose setting element 60 and housing 10 to lock the dose setting element 60 rotationally. This ensures that if a dose has been dialled, the drive spring 90 cannot return the dose setting element 60 to its zero position during the reset operation. The spline interface 64, 71 between the dose setting element 60 and button 70 remains engaged, preventing rotation of the button 70 while in the reset condition.

The user can then fit a new cartridge 100 into the cartridge holder 20, and the bearing 140 and piston rod 30 be pushed back into the mechanism. As the piston rod 30 is returned into the mechanism, a rotation in the piston rod 30 is generated due to the housing 10 thread interface.

This piston rod 30 rotation causes the drive sleeve 40 to rotate due to their spline interface, which acts to backwind the last dose nut 50 towards its start position.

Towards the end of reset, the cartridge holder 20 contacts the housing 10 and at this point the bearing 140, piston rod 30 and last dose nut 50 have reached a fully reset position. Pure rotation of the cartridge holder 20 to a locked position then acts to move the reset plate 150 (and consequently dose setting element 60) in a proximal direction, reengaging splines with the drive sleeve 40 and clutch plate 120.

In the current embodiment as described above, pressing of the button 70 with the device in the reset condition will cause re-engagement of splines 41, 151 between the drive sleeve 40 and reset plate 150, preventing any further actions to reset the device until the button 70 is released.

Figure 13:
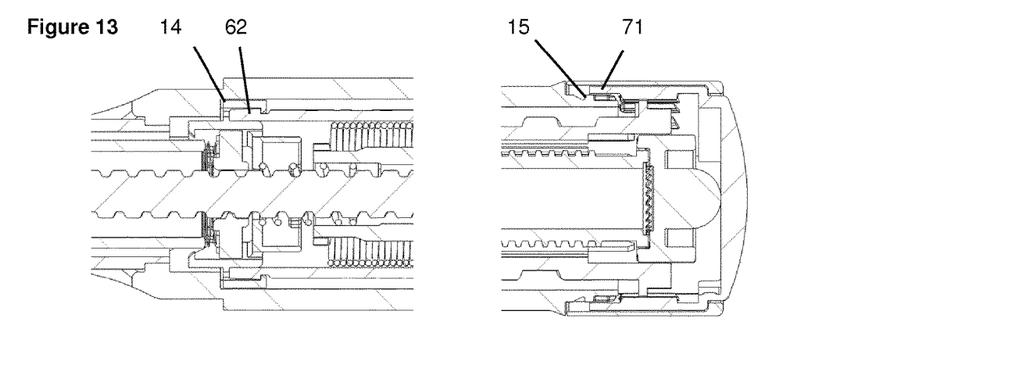
FIG. 13 shows details of an alternative embodiment of drug delivery device.

This may be prevented by controlling the relative rotational position of spline interfaces such that in the reset condition, when the dose setting element 60 is rotationally locked to the housing 10, the dose element 60 rotates the button 70 so that the splines 71 axially abut the housing splines 15 and hence the button 70 cannot move axially (FIG. 13).

REFERENCE NUMERALS 10 housing
11a, b opening (window, aperture)
12 flange-like inner wall
13 strip
14 spline
15 spline
20 cartridge holder
30 piston rod (lead screw)
31 outer thread
40 drive sleeve
41 teeth
42 ratchet teeth
43 spline
44 thread
50 nut (last dose nut)
60 dose setting element (number sleeve, dose indicator)
61 spline
62 spline
63 thread
64 spline
65 teeth
66 ratchet
70 button
71 spline
72 clicker arm
80 dose selector
90 torsion spring
100 cartridge
110 gauge element
111 opening (window, aperture)
112 helical feature
120 clutch plate (clutch element)
121 ratchet teeth
122 teeth
130 clutch spring (trigger spring)
140 bearing
150 reset plate (reset element)
151 splines
160 cartridge holder spring
l longitudinal axis

The invention claimed is:

1. A drug delivery device for selecting and dispensing a number of user variable doses of a medicament, the device comprising: a housing; a dose setting element rotatable relative to the housing during dose setting and dose dispensing; a drive member coupled to the dose setting element via a clutch; a piston rod coupled to the housing and to the drive member; a cartridge holder removably attached to the housing and a reset element, which is axially constrained to the dose setting element; and at least one spring acting on the reset element, wherein, if the cartridge holder is detached from the housing, the reset element is axially moved relative to the housing into a position in which the dose setting element is rotationally constrained to the housing and the drive member is allowed to rotate relative to the housing.

2. The drug delivery device according to claim 1, wherein, if the cartridge holder is attached to the housing, the cartridge holder moves the reset element and the dose setting element against a bias of the at least one spring into a position in which the dose setting element is rotatable relative to the housing.

3. The drug delivery device according to claim 1, wherein the reset element is permanently rotationally constrained to the housing.

4. The drug device according to claim 1, wherein the drive member is axially movable relative to the housing between a dose setting position and a dose dispensing position, wherein in the dose setting position, the drive member is rotationally constrained to the housing via the reset element, and wherein in the dose dispensing position the drive member is rotatable relative to the reset element and the housing.

5. The drug delivery device according to claim 4, wherein the at least one spring biases the drive member into the dose setting position.

6. The drug delivery device according to claim 1, wherein the housing comprises an inwardly protruding wall with a central opening and at least one further opening, and wherein one of the cartridge holder or the reset element comprises at least one axially extending finger extending through the further opening.

7. The drug delivery device according to claim 6, wherein the inwardly protruding wall comprises an inner thread and wherein the piston rod is rotationally constrained to the drive member and comprises an outer thread engaging the inner thread.

8. The drug delivery device according to claim 6, further comprising at least one cartridge holder spring axially interposed between the cartridge holder and the inwardly protruding wall.

9. The drug delivery device according to claim 1, further comprising a drive spring interposed between the housing and the dose setting element.

10. The drug delivery device of claim 9, wherein the drive spring is a torsion spring.

11. The drug delivery device according to claim 1 further comprising a gauge element radially interposed between the housing and the dose setting element, wherein the gauge element is axially movable relative to the housing and in threaded engagement with the dose setting element.

12. The drug delivery device according to claim 11 wherein the housing comprises at least one aperture, wherein the gauge element comprises at least one aperture, wherein the dose setting element comprises markings on its outer surface, and wherein at least one of the markings is visible through the aperture in the gauge element and the aperture in the housing during dose setting and dose dispensing.

13. The drug delivery device according to 11, wherein the gauge element comprises a minimum dose rotational stop and a maximum dose rotational stop and the dose setting element comprises a minimum dose rotational counter stop and a maximum dose rotational counter stop.

14. The drug delivery device according to claim 1, further comprising a slipping clutch comprising a first ring of clutch teeth on the drive member and a second ring of clutch teeth on a clutch plate, wherein the clutch plate is rotationally constrained to the dose setting element during dose setting and dose dispensing.

15. The drug delivery device according to claim 14, wherein the at least one spring biases the drive member into abutment with the clutch plate, and wherein, if the cartridge holder is detached from the housing, the at least one spring biases the dose setting element into an axial position relative to the clutch plate in which the clutch plate and the dose setting element are rotationally de-coupled.

16. The drug delivery device according to claim 1, further comprising a cartridge containing a medicament.

17. The drug delivery device of claim 16, wherein the medicament comprises a pharmaceutically active compound.

* * * * *

UNITED STATES PATENT AND TRADEMARK OFFICE
CERTIFICATE OF CORRECTION

PATENT NO. : 10,350,360 B2
APPLICATION NO. : 15/517875
DATED : July 16, 2019
INVENTOR(S) : Zoe Georgina Eardley and Paul Richard Draper Page 1 of 1

It is certified that error appears in the above-identified patent and that said Letters Patent is hereby corrected as shown below:

On the Title Page

In the Abstract:
Column 2, Line 13, under "ABSTRACT", delete "onto" and insert -- into --.

In the Claims

Column 18, Line 52, Claim 13, after "to", insert -- claim --.

Signed and Sealed this
Twenty-sixth Day of November, 2019

Andrei Iancu
*Director of the United States Patent and Trademark Office*